(12) United States Patent
Chang et al.

(10) Patent No.: US 6,777,673 B2
(45) Date of Patent: Aug. 17, 2004

(54) ION TRAP MASS SPECTROMETER

(75) Inventors: Huan-Cheng Chang, Taipei (TW); Wen-Ping Peng, Hou-long Town (TW); Yong Cai, Zhengzhou (CN); Shan-Jen Kuo, Ban-qiao (TW)

(73) Assignee: Academia Sinica, Taipei (TW)

( * ) Notice: Subject to any disclaimer, the term of this patent is extended or adjusted under 35 U.S.C. 154(b) by 30 days.

(21) Appl. No.: 10/034,459

(22) Filed: Dec. 28, 2001

(65) Prior Publication Data

US 2003/0122070 A1 Jul. 3, 2003

(51) Int. Cl.$^7$ .......................... B01D 54/44; H01J 49/00
(52) U.S. Cl. ................. 250/290; 250/281; 250/293
(58) Field of Search .................. 250/290, 281, 250/282, 292, 293

(56) References Cited

U.S. PATENT DOCUMENTS

| | | | |
|---|---|---|---|
| 4,383,171 A | 5/1983 | Sinha et al. ............. 250/282 |
| 4,540,884 A | 9/1985 | Stafford et al. .......... 250/282 |
| 4,749,860 A | 6/1988 | Kelley et al. ............ 250/282 |
| 5,170,054 A | 12/1992 | Franzen ................. 250/292 |
| 5,270,542 A | 12/1993 | McMurry et al. ......... 250/288 |
| 5,300,772 A * | 4/1994 | Buttrill, Jr. ............. 250/282 |
| 5,382,794 A | 1/1995 | Downey et al. .......... 250/288 |
| 5,399,857 A | 3/1995 | Doroshenko et al. ..... 250/292 |
| 5,457,315 A * | 10/1995 | Wells et al. ............. 250/282 |
| 5,572,025 A | 11/1996 | Cotter et al. ............ 250/292 |
| 5,572,035 A * | 11/1996 | Franzen ............... 250/396 R |
| 5,640,010 A | 6/1997 | Twerenbold ............. 250/281 |
| 5,681,752 A | 10/1997 | Prather ................. 436/173 |
| 5,696,376 A * | 12/1997 | Doroshenko et al. ..... 250/292 |
| 5,736,741 A * | 4/1998 | Bertsch et al. .......... 250/288 |
| 5,770,857 A * | 6/1998 | Fuerstenau et al. ...... 250/281 |
| 5,783,824 A * | 7/1998 | Baba et al. ............. 250/281 |
| 5,880,466 A | 3/1999 | Benner ................. 250/281 |
| 5,998,215 A | 12/1999 | Prather et al. ........... 436/173 |
| 6,040,574 A | 3/2000 | Jayne et al. ............. 250/288 |
| 6,157,030 A | 12/2000 | Sakairi et al. ........... 250/292 |
| 6,188,065 B1 | 2/2001 | Takada et al. ........... 250/288 |
| 6,194,716 B1 | 2/2001 | Takada et al. ........... 250/292 |
| 6,316,769 B2 | 11/2001 | Takada et al. ........... 250/292 |
| 6,452,168 B1 * | 9/2002 | McLuckey et al. ....... 250/292 |

OTHER PUBLICATIONS

Bohren and Huffman, "Absorption and scattering of light by small particles" (Table of Contents only) (1983).

Bruce et al., "Trapping, Detection, and Mass Measurement of Individual Ions in a Fourier Transform Ion Cyclotron Resonance Mass Spectrometer", *J. Am. Chem. Soc.*, 116:7839–7847 (1994).

Cheng et al., "Charge–State Shifting of Individual Multiply–Charged Ions of Bovine Albumin Dimer and Molecular Weight Determination Using an Individual–Ion Approach", *Anal. Chem.*, 66:2084–2087 (1994).

Cleven et al., "Radial Distributions and Ejection Times of Molecular Ions in an Ion Trap Mass Spectrometer: A Laser Tomography Study of Effects of Ion Density and Molecular Type", *J. Phys. Chem.*, 100:40–46 (1996).

(List continued on next page.)

*Primary Examiner*—Jack Berman
*Assistant Examiner*—Kalimah Fernandez
(74) *Attorney, Agent, or Firm*—Fish & Richardson P.C.

(57) ABSTRACT

A mass spectrometer that includes an ion source, an ion trap, and a light detection module. The ion trap has two end-cap electrodes and a ring electrode. The ring electrode is positioned relative to the end-cap electrodes to confine a charged particle from the ion source within a confinement region when an audio frequency voltage having a first amplitude is applied between the ring electrode and the two end-cap electrodes. The charged particle is ejected from the ion trap when the audio frequency voltage increases to a second amplitude. The light detection module includes a light source that illuminates the ejected particle and a light detector that detects light scattered from the ejected particle.

24 Claims, 7 Drawing Sheets

OTHER PUBLICATIONS

Cox et al., "Mass shifts and local space charge effects observed in the quadruple ion trap at higher resolution", *International Journal of Mass Spectrometry and Ion Processes*, 144:47–65 (1995).

Davis, "A History of Single Aerosol Particle Levitation", *Aerosol Science and Technology*, 26:212–254 (1997).

Fenn et al., "Electrospray Ionization for Mass Spectrometry of Large Biomolecules", *Science*, 246:64–71 (1989).

Fuerstenau and Benner, "Molecular Weight Determination of Megadalton DNA Electrospray Ions Using Charge Detection Time–of–flight Mass Spectrometry", *Rapid Communications in Mass Spectrometry*, 9:1528–1538 (1995).

Fuerstenau et al., "Mass Spectrometry of an Intact Virus", *Angew. Chem. Int. Ed.*, 40:542–544 (2001).

Gerlich et al., "Experiments with Trapped Ions and Nanoparticles", Faculty of Natural Science, Technical University of Chemnitz, Germany, 149–154.

Hars and Tass, "Application of quadrupole ion trap for the accurate mass determination of submicron size charged particles", *J. Appl. Phys.*, 77:4245–4250 (1995).

Hunter and Lias, "Evaluated Gas Phase Basicities and Proton Affinities of Molecules: An Update", *J. Phys. Chem. Ref. Data*, 27:413–416 (1998).

Kaiser, Jr. et al., "Operation of a Quadrupole Ion Trap Mass Spectrometer to Achieve High Mass/Charge Ratios", *Int. J. Mass Spectrom. Ion Processes*, 106:79–115 (1991).

Londry et al., "Enhanced Mass Resolution in a Quadrupole Ion Trap", *Rapid Communication in Mass Spectrometry*, 7:43–45 (1993).

March, "Quadrupole ion trap mass spectrometry: a view at the turn of the century", *Int. J. Mass Spectrom.*, 200:285–312 (2000).

March and Hughes, "Quadrupole Storage Mass Spectrometry", *Chemical Analysis*, 102 (Table of Contents only) (1989).

March and Londry, "Theory of Quadrupole Mass Spectrometry", *Practical Aspects of Ion Trap Mass Spectrometry*, 1:25–48 (1995).

McLuckey et al., "Novel quadrupole ion trap methods for characterizing the chemistry of gaseous macro–ions", *Int. J. Mass Spectrom.*, 200:137–161 (2000).

Noble and Prather, "Real–Time Single Particle Mass Spectrometry: A Historical Review of a Quarter Century of the Chemical Analysis of Aerosols", *Mass Spectrometry*, 19:248–250 (2000).

Nohmi and Fenn, "Electrospray Mass Spectrometry of Poly-(ethylene glycols) with Molecular Weights up to Five Million", *J. Am. Chem. Soc.*, 114:3241–3246 (1992).

Schlemmer et al., "Nondestructive high–resolution and absolute mass determination of single charged particles in a three–dimensional quadrupole trap", *Journal of Applied Physics*, 90:5410–5418 (2001).

Schlunegger et al., "Frequency Scan for the Analysis of High Mass Ions Generated by Matrix–assisted Laser Desorption/Ionization in a Paul Trap", *Rapid Commun. Mass Spectrom.*, 13:1792–1796 (1999).

Syka, "Nonlinear Ion Traps", *Practical Aspects of Ion Trap Mass Spectrometry*, 1:153–166.

Tang and Gomez, "On the structure of an electrostatis spray of monodisperse droplets", *Phys. Fluids*, 6:2317–2332 (1994).

Van Berkel et al., "Electrospray Ionization Combined with Ion Trap Mass Spectrometry", *Anal. Chem*, 62:1284–1286 (1990).

Wang and Franzen, "The non–linear ion trap. Part 3. Multipole components in three types of practical ion trap", *Int. J. Mass. Spectrom. Ion Processes*, 132:155–157 (1994).

Winter and Ortjohann, "Simple demonstration of storing macroscopic particles in a "Paul trap"", *Am. J. Phys*, 59:807–813 (1991).

Dahneke, "Aerosol Beam Spectrometry", *Nature Physical Science*, 244:54–55 (1973).

Dahneke amd Flachsbart, "An Aerosol Beam Spectrometer", Aerosol Science, 3:345–349 (1972).

Gard et al., "Real–Time Analysis of Individual Atmospheric Aerosol Particles: Design and Performance of a Portable ATOFMS", *Anal. Chem.*, 69:4083–4091 (1997).

Kaufman et al., "Macromolecule Analysis Based on Electrophoretic Mobility in Air: Globular Proteins", *Anal. Chem.*, 68:1895–1904 (1996).

March, "An Introduction to Quadrupole Ion Trap Mass Spectrometry", *Journal of Mass Spectrometry*, 32:351–369 (1997).

Salt et al., "Aerodynamic Particle Sizing versus Light Scattering Intensity Measurement as Methods for Real–Time Particle Sizing Coupled with Time–of–Flight Mass Spectrometry", *Anal. Chem.*, 68:230–234 (1996).

Schreiner et al., "Chemical Analysis of Polar Stratospheric Cloud Particles", *Science*, 283:968–970 (1999).

Suess and Prather, "Mass Spectrometry of Aerosols", *Chem. Rev.*, 99:3007–3035 (1999).

Wuerker et al., "Electrodynamic Containment of Charged Particles", *Journal of Applied Physics*, 30:342–349 (1959).

Wuerker et al., "Electrodynamic Containment of Charged Particles by Three–Phase Voltages", received by journal on Oct. 17, 1958.

* cited by examiner

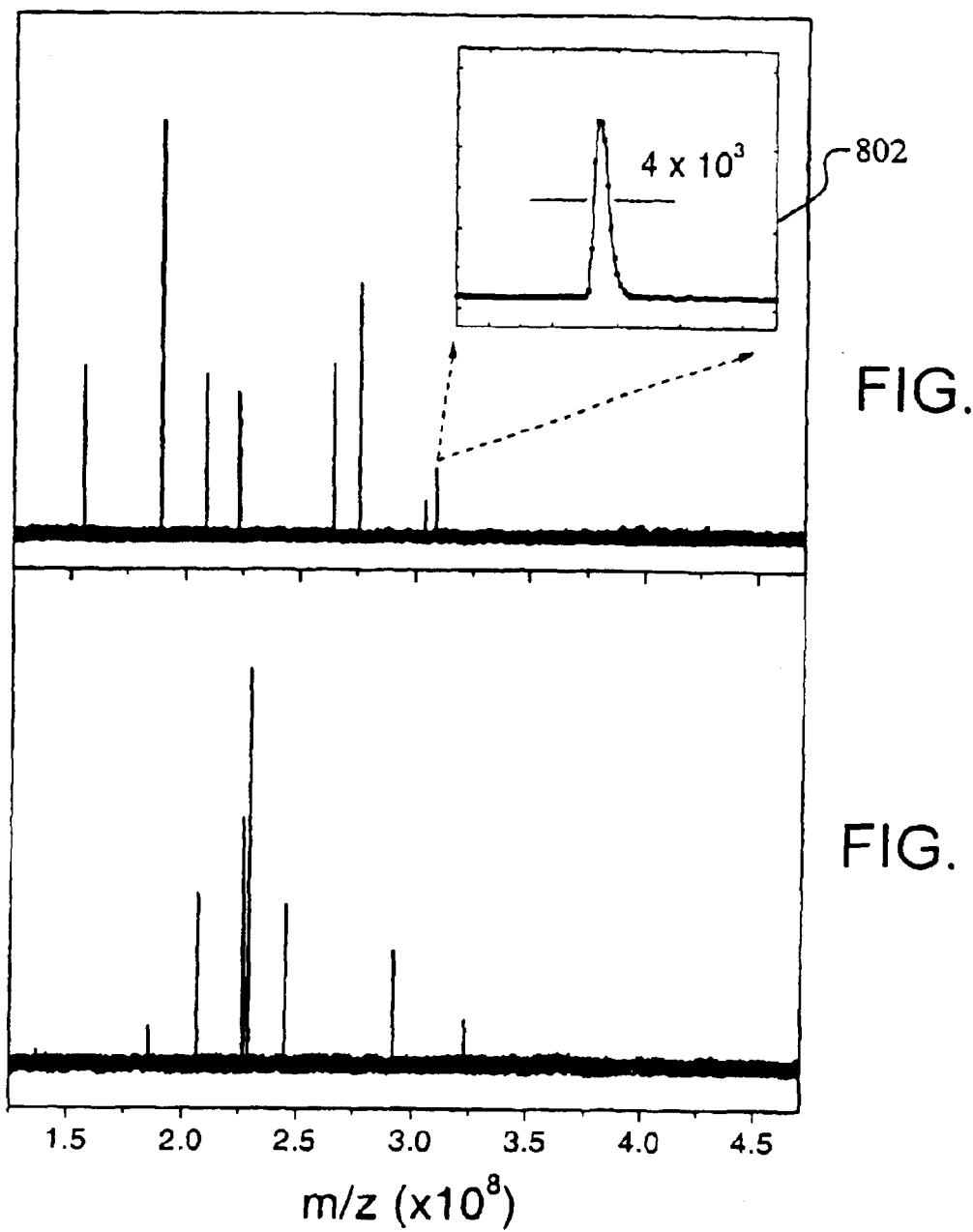

ION TRAP MASS SPECTROMETER

TECHNICAL FIELD

This invention relates to ion trap mass spectrometer.

BACKGROUND

Mass spectrometers are used to determine the identity and quantity of components that make up a solid, gas, or aqueous sample. A mass spectrometer typically uses the ratio of the ion mass (m) to its charge (z) for analyzing and separating ions. The ion mass is typically expressed in atomic mass units or Daltons (Da) and the ion charge (z) represents the number of electric charges of the ion. One type of mass spectrometer is the quadrupole ion trap mass spectrometer (QITMS), which can be used for analyzing the mass of atomic, molecular and cluster ions. A QITMS typically has a ring electrode and two end-cap electrodes. In operation, a fixed radio-frequency (e.g., approximately 1 MHz) voltage is applied between the ring electrode and the end-cap electrodes to create a time-varying electromagnetic field to confine the ions within a confinement region.

Another type of mass spectrometer is the aerosol time-of-flight mass spectrometer (ATOFMS), which can be used to determine the size and chemical compositions of single aerosol particles in real time. An ATOFMS uses two laser beams to measure the velocity of individual particles in an aerosol beam. The particle's aerodynamic size is determined from the measured velocity. The chemical composition of each particle is then analyzed using a laser desorption/ionization time-of-flight mass spectrometer. The ATOFMS provides a mass spectrum of the chemical compositions of the particles being analyzed, but reveals little information about the mass/charge ratio of the particles themselves.

SUMMARY

In general, in one aspect, the invention features an ion trap that includes two end-cap electrodes and a ring electrode. The ring electrode is positioned between the two end-cap electrodes to form a confinement region. An ion (or a charged particle) from an ion source is confined within the confinement region when an audio frequency voltage is applied between the ring electrode and the end-cap electrodes. The ion is ejected from the ion trap when the amplitude of the audio frequency voltage is increased.

Implementations of the invention may include one or more of the following features. One of the end-cap electrode includes an ion entrance aperture to allow the charged particle to enter into the confinement region, and the other end-cap electrode includes an ion ejection aperture to allow the charged particle to exit the confinement region. The ring electrode includes an observation aperture to allow observation of the movement of the charged particle within the confinement region. The ion trap is used with a light detection module to detect light scattered from the charged particle after it is ejected from the ion trap. The ion source is positioned above the ion trap and includes a needle, a capillary, and a differential pumping region. The needle is aligned along a vertical axis above the capillary, and the capillary is aligned along the vertical axis above the differential pumping region. The capillary and the differential pumping region are connected to electric ground, and the needle is connected to a DC voltage. The audio frequency voltage is in a frequency range between about 50 and 2000 hertz. The ion has a mass in the range between about 1 mega-dalton and 10,000 mega-daltons. The audio frequency voltage has an amplitude in the range between about 400 and 1700 volts.

In general, in another aspect, the invention features a method that includes introducing a charged particle into an ion trap having two end-cap electrodes and a ring electrode positioned between the end-cap electrodes. An audio frequency voltage having a first amplitude is applied between the ring electrode and the end-cap electrodes to generate an electromagnetic field that confines the charged particle within a confinement region. The amplitude of the audio frequency voltage is increased to a second amplitude to eject the charged particle from the ion trap.

Implementations of the invention may include one or more of the following features. A secular frequency of the motion of the charged particle inside the confinement region is measured. A mass-to-charge ratio of the charged particle is calculated based on the second amplitude of the audio frequency voltage and the measured secular frequency.

In general, in another aspect, the invention features a mass spectrometer that includes an ion source, and an ion trap, and a light detection module. The ion trap has two end-cap electrodes and a ring electrode. The ring electrode is positioned relative to the end-cap electrodes to confine a charged particle from the ion source within a confinement region when an audio frequency voltage having a first amplitude is applied between the ring electrode and the two end-cap electrodes. The charged particle is ejected from the ion trap when the audio frequency voltage increases to a second amplitude. The ejected charged particle is detected by the light detection module.

In general, in another aspect, the invention features a method that includes introducing a charged particle into an ion trap of a mass spectrometer, the ion trap having two end-cap electrodes and a ring electrode positioned between the two end-cap electrodes. An audio frequency voltage having a frequency of f and an amplitude of $V_{ac}$ is applied between the ring electrode and the end-cap electrodes to generate an electromagnetic field that confines the charged particle within a confinement region. A secular frequency $\omega$ representing the oscillation frequency of the motion of the charged particle within the confinement region is measured. The amplitude of the audio frequency voltage is then increased to a second amplitude $V_{eject}$ to eject the charged particle from the ion trap. A calibration parameter $q_{eject}$ is calculated based on $V_{ac}$, $V_{eject}$, f, and $\omega$. The calibration parameter is used to calculate a mass-to-charge ratio of other charged particles that are introduced into the ion trap and ejected from the ion trap.

Implementations of the invention may include one or more of the following features. The calibration parameter $q_{eject}$ is calculated using the equation $$q_{eject} = \frac{V_{eject}}{V_{ac}} \frac{4\sqrt{2}\,\omega}{\Omega},$$

where $\Omega = 2\pi f$.

The radius r of the ring electrode is measured, and a mass-to-charge ratio of another charged particle is calculated using the equation $$m/z = \frac{4V_{eject2}}{q_{eject}r^2\Omega^2},$$

where $V_{eject2}$ is the amplitude of the audio frequency voltage when the other charged particle is ejected from the ion trap.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 8a and 8b are graphs showing single-particle mass spectra of amino-polystyrene particles. FIG. 8a also shows an enlarged view of a peak in the mass spectrum.

Like reference symbols in the various drawings indicate like elements.

DETAILED DESCRIPTION

Construction of a Single-Particle Mass Spectrometer

Figure 1:
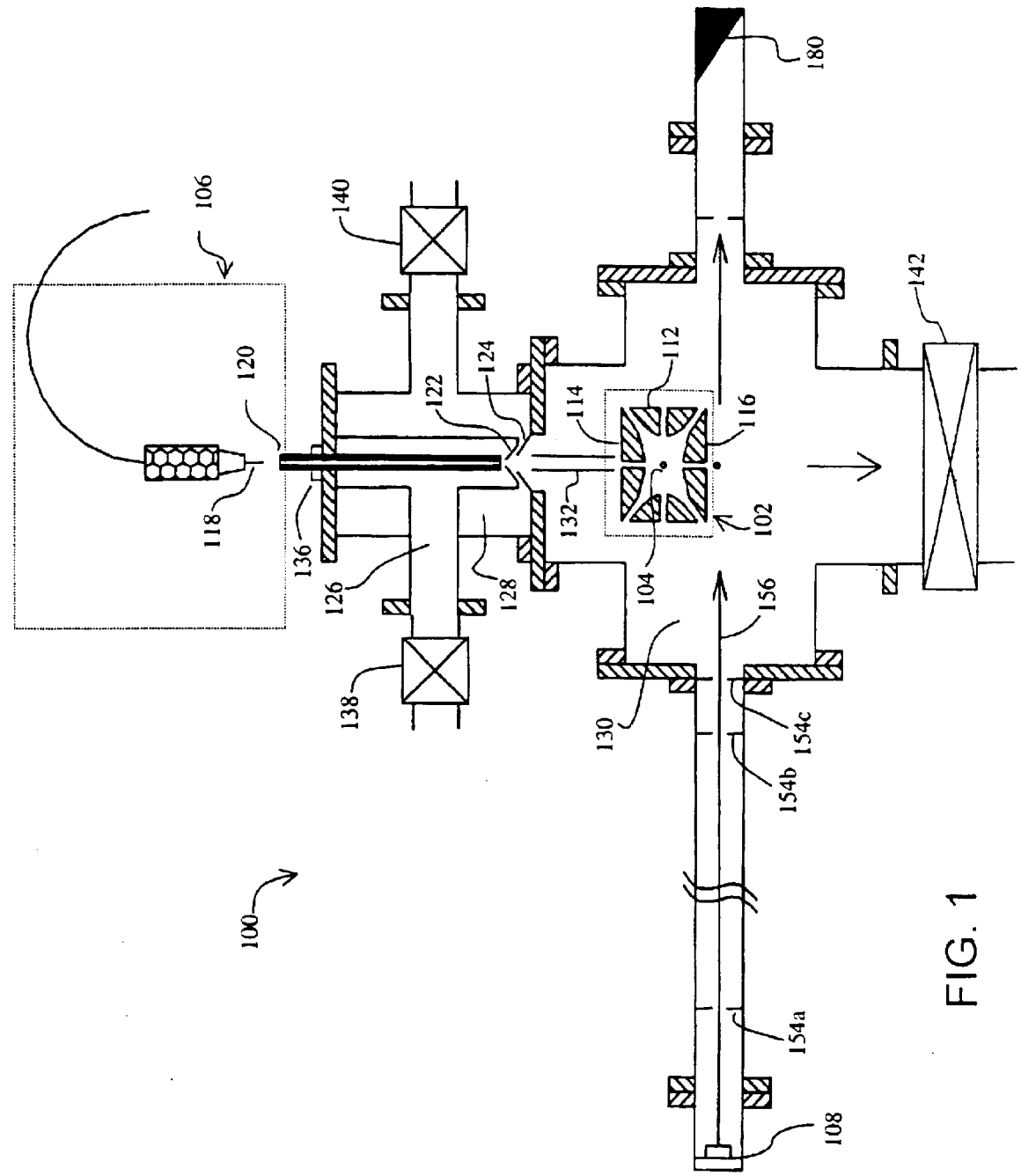
FIG. 1 is a schematic diagram of an ion trap mass spectrometer.
Figure 2:
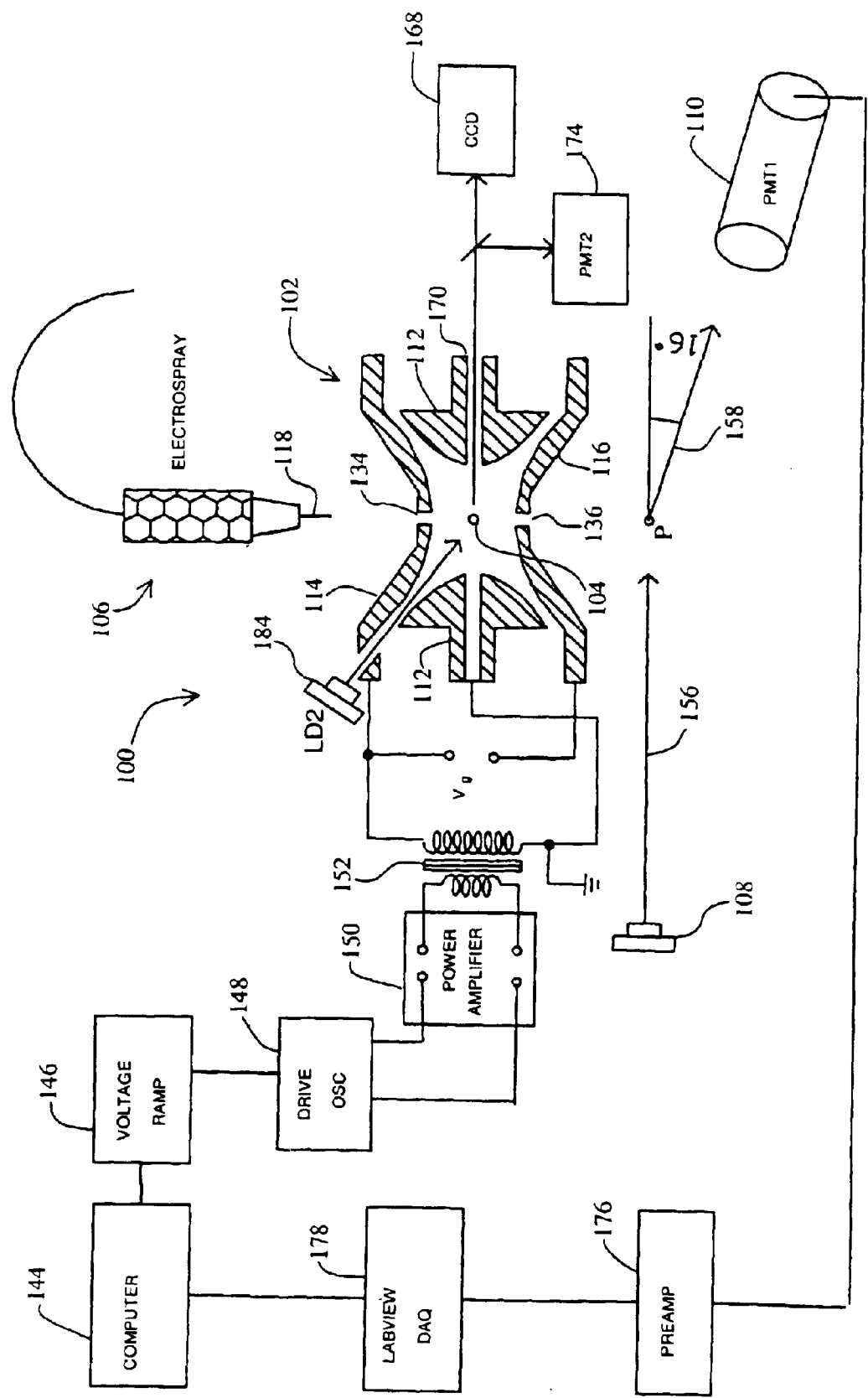
FIG. 2 is a schematic diagram of an ion trap and supporting devices used in the operation of the ion trap.

Referring to FIGS. 1 and 2, a single-particle mass spectrometer 100 includes an ion trap 102 that traps a charged particle 104 generated by an electrospray ionization source 106 (ion trap 102 and source 106 are shown enclosed in dashed lines). Ion trap 102 includes a central, hyperbolic cross-section, ring electrode 112 located between an upper hyperbolic end-cap electrode 114 and a lower hyperbolic end-cap electrode 116. Charged particle 104 is trapped inside ion trap 102 when an audio frequency (e.g., 50–2000 Hz) voltage having an amplitude $V_{ac}$ is applied between ring electrode 112 and end-cap electrodes 114 and 116. Ring electrode 112 is connected to electric ground. As the amplitude $V_{ac}$ of the audio frequency voltage is increased to a value $V_{eject}$, the motion of charged particle 104 inside ion trap 102 becomes unstable and charged particle 104 is ejected from ion trap 102. The ejected charged particle 104 is illuminated by a light beam 156 generated by a laser diode 108, and a photo-multiplier tube 110 is used to detect light scattered from charged particle 104. As will be described in more detail below, the mass-to-charge ratio of charged particle 104 can be determined from $V_{eject}$, the audio frequency voltage, and the radius of the ring electrode 112.

Electrospray Ionization Source

Electrospray ionization source 106 acts as a single particle generator and brings submicron-sized particles into a gas phase suitable for mass spectral analysis. Electrospray ionization source 106 includes a needle 118 (with a diameter of about 200 μm) that is connected to a 4 kV DC voltage. A solution containing particles to be analyzed is vaporized after passing through needle 118, and the particles are ionized by the high voltage applied to the needle so that the particles carry electric charge. The charged particles 104 pass through a capillary 120 (with an inner diameter of about 500 μm) that is connected to electric ground and mounted on a quick connector 136. The charged particles 104 pass through the capillary 120 to a first skimmer 122 having an orifice diameter of about 700 μm.

The first skimmer 122 separates differentially pumped chambers 126 and 128. A mechanical pump 138 having a pumping capacity of about 12 liters per second maintains the pressure inside chamber 126 at about 1 Torr. A suitable mechanical pump is model number E2M40 from Edwards High Vacuum International, West Sussex, U.K. A roots pump 140 having a pumping capacity of about 50 liters per second maintains the pressure inside chamber 128 at about 1 mTorr. A suitable roots pump is model number LS80L2 from Alcatel Vacuum Technology Division 98, Annecy-France. The pressure difference between chambers 126 and 128 generates a gas flow that carries the charged particles 104 through the first skimmer 122 and through a second skimmer 124 (with an orifice diameter of about 1.5 mm) into the ion trap chamber 130. A turbomolecular pump 142 having a pumping capacitor of about 250 liters per second maintains the pressure inside chamber 130 at about $7\times10^{-5}$ Torr. A suitable turbomolecular pump is model number TH253M from Osaka Vacuum, Osaka, Japan.

The charged particles 104 enter a beam tube 132 inside chamber 130, and is directed towards an entrance hole 134 of the ion trap 102 for electrodynamic confinement. Once the charged particles 104 are confined within ion trap 102, the electrospray ionization source 106 is turned off, and the capillary 120 is sealed. The turbomolecular pump 142 then maintains a pressure at about $2\times10^{-6}$ Torr inside chamber 130, and the pressures inside chambers 126 and 128 are about 5 mTorr and 0.1 mTorr, respectively. This electrospray ionization source design has the advantage that charged particles of submicron size can be substantially dispersed in the gas phase so that subsequent measurements are conducted on individual charged particles rather than agglomerates of charged particles.

Movement of the charged particles 104 through capillary 120, skimmer 122, skimmer 124, and beam tube 132 is dominated by aerodynamics rather than by electrostatics. Capillary 120 and beam tube 132, as well as first and second skimmers 122, 124 are connected to electric ground. A vertical beam axis is used in this design to prevent the particles from hitting the walls of the beam tubes and skimmers due to influence from gravity.

ION TRAP

The ion trap 102 is mounted on a solid support (not shown in the figure) inside chamber 130. Chamber 130 may, for example, have a diameter of 6 inches. An example of ion trap 102 is a quadrupole ion trap modified from commercially available ion trap detectors (e.g., model C-1251 from R. M. Jordan Company Inc., Grass Valley, Calif.) so that the distance $z_0$ between the center of the ion trap to an inner surface of the upper end-cap electrode 114 (or the lower end-cap electrode 116) is about 7.07 mm. Six holes are drilled on the ring electrode and end-caps. The holes are located on three perpendicular axes that intersect at the center of the ion trap 102. A hole 134 having a diameter of about 3.1 mm is drilled on the upper end-cap electrode 114 to provide a pathway for the charged particles 104 to enter the ion trap 102. A hole 136 also having a diameter of about 3.1 mm is drilled on the lower end-cap electrode 116 to provide a pathway for ejected charged particles 104 to leave the ion trap 102. Four holes having diameters of about 3.8 mm are drilled on the ring electrode 112 to allow illumination and observation of the particles inside ion trap 102.

A computer 144 controls a voltage ramp generator 146, which in turn controls the amplitude of the signals generated by a drive oscillator 148. The drive oscillator 148 can be, for example, a synthesized function generator that generates an audio frequency sinusoidal voltage signal having a frequency that is controllable by a user, for example, with computer 144. The signals generated by drive oscillator 148 is amplified by an audio frequency power amplifier 150, which drives the input terminals of a high-voltage transformer 152. The transformer 152 increases the voltage amplitude of the signals from power amplifier 150. An audio frequency voltage having an amplitude $V_{ac}$ is generated at the output terminals of the transformer 152, which are coupled to electric ground and the upper end-cap electrode 114. The ring electrode 112 is connected to electric ground, and a small DC voltage ($V_g$) is applied between the upper and lower end-cap electrodes 114, 116 to counteract gravitational forces.

To obtain a mass spectrum of the charged particles 104, ion trap 102 is operated under a mass-selective instability mode where the voltage amplitude $V_{ac}$ is scanned from a lower voltage value to a higher voltage value so that charged particles of different mass-to-charge ratios exit the trap in sequence (a charged particle having a lower m/z value exits first). Before the voltage scans, the chamber 130 (and also the region inside ion trap 102) is back-filled with He buffer gas to 1 mTorr to retain the charged particles 104 near the center of ion trap 102 while also reducing the radial amplitude of the oscillatory motions of charged particles 104. The amplitude $V_{ac}$ of the audio frequency voltage is varied from about 400 volts to about 1700 volts as the charged particles 104 are ejected from the ion trap 102 in sequence. The frequency (f) of the audio frequency voltage may be, for example, between about 50 to 2000 Hz. The trapping time of the charged particles prior to ejection may be, for example, about 30 seconds, and the total voltage scan time may be, for example, about 12 seconds.

Scattered Light Detection Module

Detection of scattered laser light is used to identify charged particles 104 that are ejected out of the ion trap 102. Laser diode 108 (e.g., a 50 mW laser diode, model ML101J10 available from Semiconductor Division, Mitsubishi Electric Co., Taiwan) generates a collimated laser beam 156 (e.g., with a wavelength λ=685 nm and a beam size of 4.5×2.2 mm$^2$). One dimension (4.5 mm) of the laser beam is sufficiently large to ensure that all the ejected charged particles are detected when they are ejected out of ion trap 102 through hole 136 on the lower end-cap electrode 116. The power density at the point of light scattering can be, for example, 10 kW/m$^2$. The laser diode 108 is mounted on a 2.75 inch conflat flange inside chamber 130 and situated about 1 meter away from a location P where the ejected particles will be illuminated by the laser beam. Light baffles 154a, 154b, 154c with apertures of 8 mm, 10 mm, and 12 mm, respectively, in diameter are positioned between laser diode 108 and location P to minimize background signals arising from scattering and reflection of the laser beam from observation windows or walls of the chamber 130. A light trap 180 is used to absorb the portion of the laser beam 156 not scattered by charged particle 104.

Figure 3:
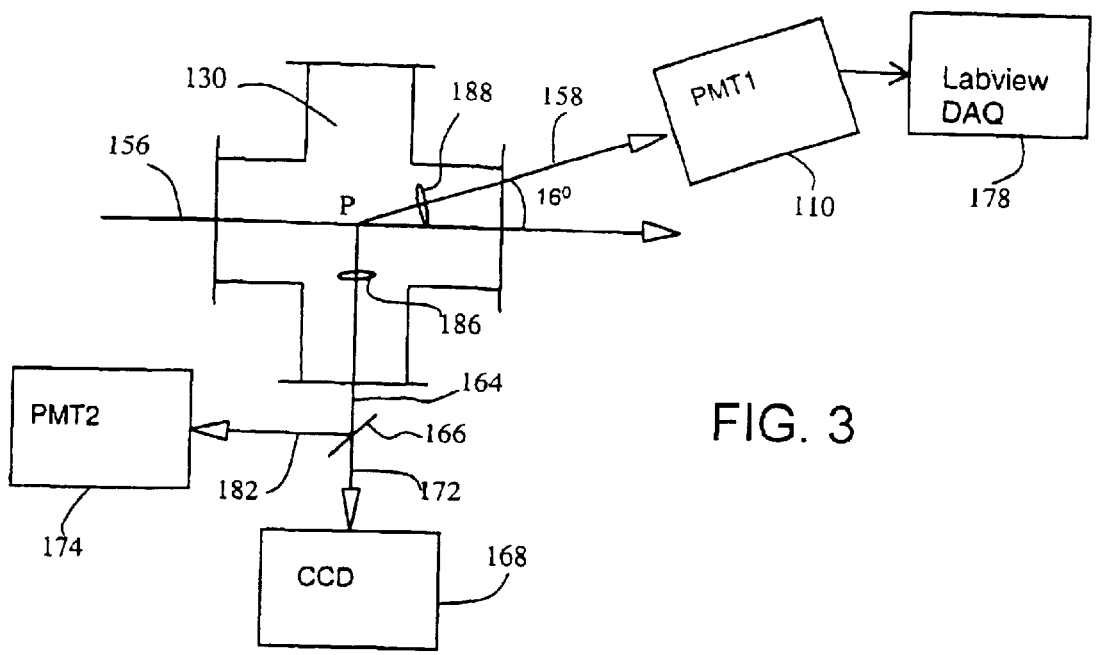
FIG. 3 is a top view of a chamber of the ion trap mass spectrometer and devices used to detect charged particles inside the chamber.

Light is scattered by the ejected particles as they pass through the collimated laser beam 156. FIG. 3 shows a top view of chamber 130. A convex lens 188 of about 25 mm in diameter is positioned about 60 mm away from the location P to focus scattered light having a forward scattering angle of 16°. The focused scattered light passes through an observation window (not shown in the figure) to a photomultiplier tube 110. A suitable photomultiplier tube is model R928 from Hamamatsu Photonics K.K., Shizuoka-Ken, Japan. Using this method, individual charged particles as small as, e.g., 100 nm, can be detected.

Photomultiplier tube 110 generates an analog voltage signal representing the intensities of the scattered light. The analog voltage signal is amplified by a pre-amplifier 176. The amplified analog voltage signal is then sent to a data acquisition board 178, such as model AT-MIO-16E-10 from National Instruments, Austin, Tex. The data acquisition board converts the analog voltage signal into a digital format through a LabView program (also available from National Instruments) that can be processed by computer 144.

Calibration of the Single-Particle Mass Spectrometer

To calibrate a mass spectrum generated from the mass spectrometer described above, ion trap 102 is used as an electrodynamic balance to determine the m/z value of a single charged particle and use it as a calibrant for later measurements. This allows the mass spectrometer to be calibrated without the use of external references. This approach can be used to calibrate measurements from audio frequency ion traps that measure charged particles with mass-to-charge ratios greater than 10$^6$.

Figure 4:
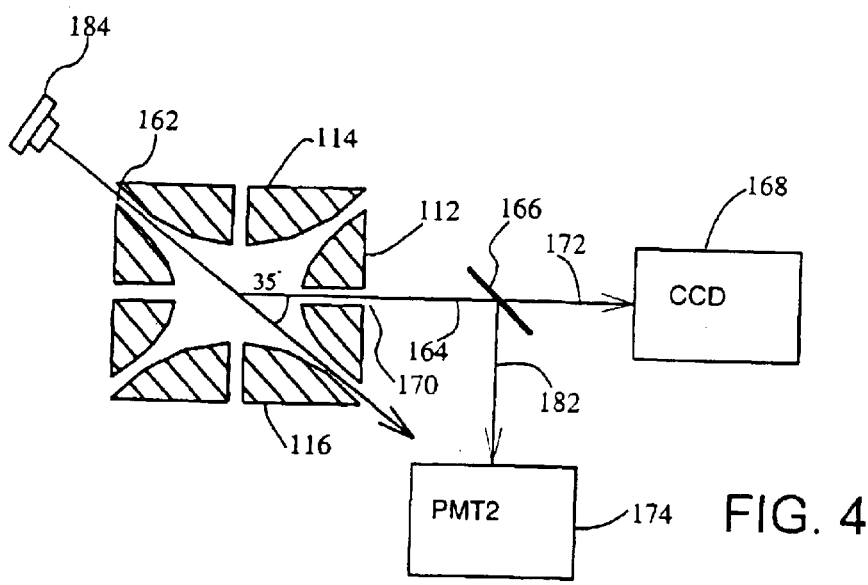
FIG. 4 is a side view of an ion trap and devices used to detect charged particles within the ion trap.

Referring to FIG. 4, when mass spectrometer 100 is operating in a calibration mode, a light beam 160 from a laser diode 184 is introduced into the ion trap 102 through a gap 162 between the upper end-cap electrode 114 and the ring electrode 112. Laser diode 108 can have the same characteristics as laser diode 108. Scattered laser light 164 from the charged particle 104 exits the ion trap 102 through the hole 170 on the ring electrode 112 and is collected by a telescope 186 (represented by the lens symbol in FIG. 3) with its optical axis directed towards the center of the ion trap. In this example, the telescope collects scattered light having a forward scattering angle of 35°. Scattered laser light 164, after passing through the telescope, is divided into two light beams 182 and 172 by a beam splitter 166. Light beam 172 is detected by a charge coupled device (CCD) camera 168, and light beam 182 is detected by a second photomultiplier tube 174 (its purpose is explained in more detail below).

Figure 5:
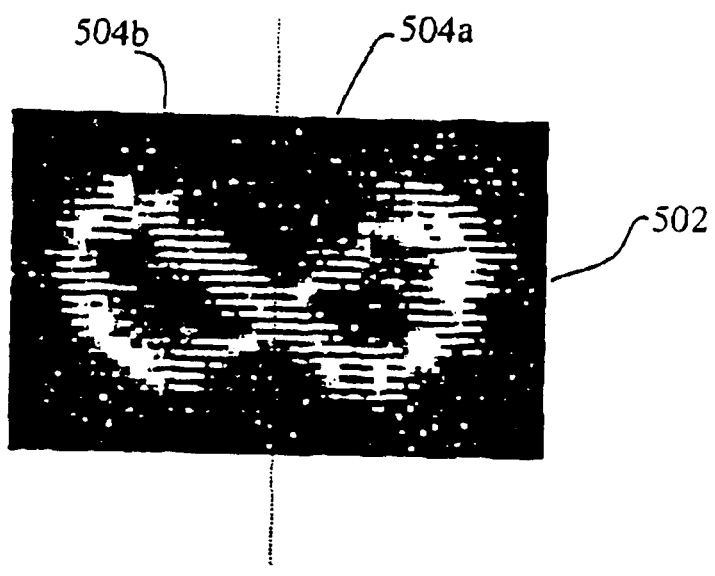
FIG. 5 is an image of the trajectory of the oscillatory motion of a single charged microparticle in the ion trap.

Referring to FIG. 5, an image 502 of the trajectory of the oscillatory motion of a single diamond nanoparticle (about 0.7 μm in diameter) confined within the trap is recorded by the CCD camera 168. The image 502 shows a near 2:1 Lissajous-type trajectory, and was obtained when $V_g$ (the voltage between the upper and lower end-cap electrodes 114, 116) was about 10 volts to compensate the influence of gravitational force on the charged diamond nanoparticle. The image shows that the diamond nanoparticle oscillates almost symmetrically above and below a central plane of the ion trap 102.

To determine the m/z value of the diamond nanoparticle, an audio frequency voltage having a frequency f=600 Hz is applied between the ring electrode and the end-cap electrodes. A secular frequency $\omega_r$ of the particle's motion in the radial direction is measured when the audio frequency voltage has a lower amplitude ($V_{ac} \approx 400$ V). Secular frequency refers to the frequency (radians per second) of an ion's oscillatory motion inside the ion trap. The radial direction refers to the direction along the radius of the ring electrode 112. The secular frequency can be measured by collecting light scattered from the charged particles as they move inside ion trap 102 using the second photomultiplier tube 174.

Figures 6, 7:
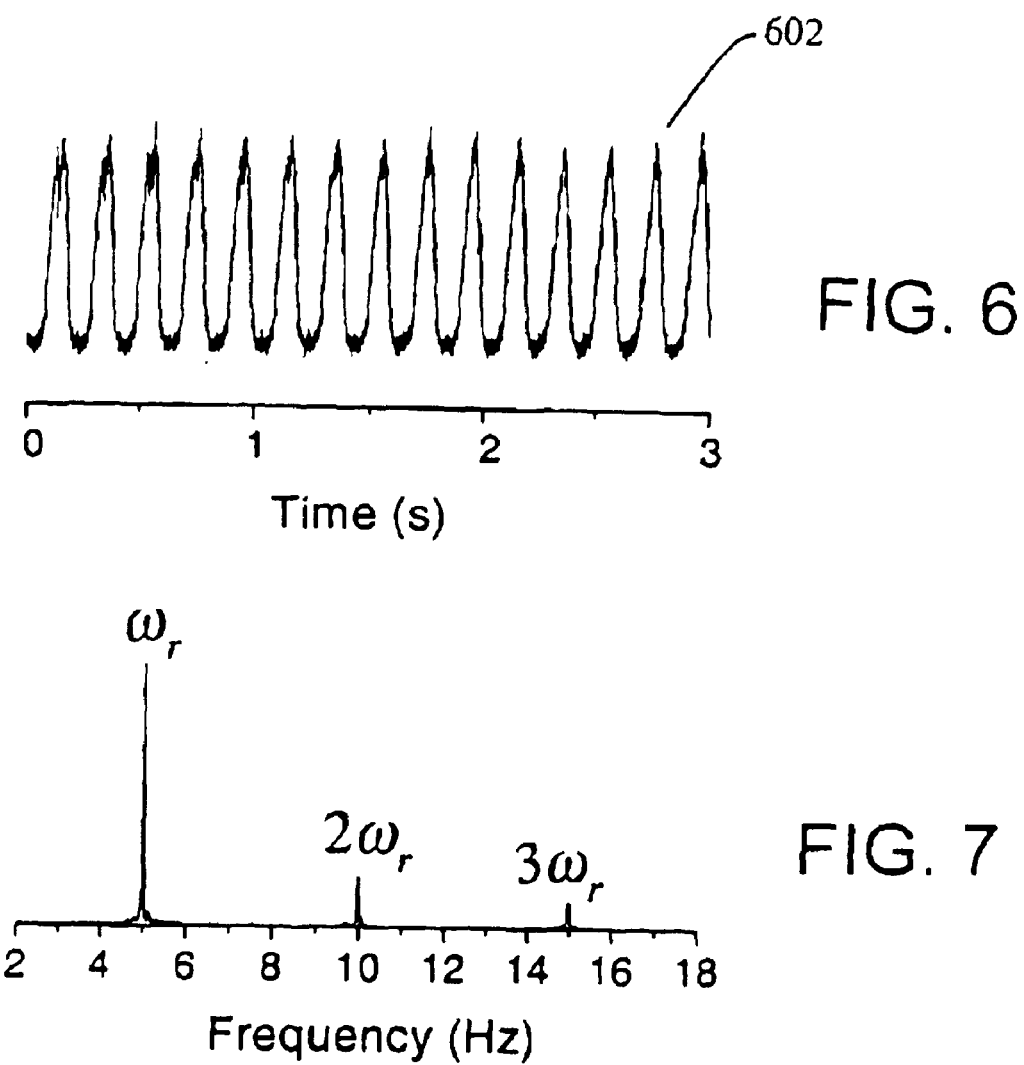
FIG. 6 is a graph showing a time-domain signal representing the intensity of light scattered by a single charged particle moving inside the ion trap as measured by a photomultiplier tube.
FIG. 7. is a graph of the Fourier transform of the time-domain signal of FIG. 6

Referring to FIG. 6 (and FIG. 4 as well), an oscillatory signal 602 is generated by photomultiplier tube 174 that captures light scattered from particles moving in and out of the region represented by the right half 504a (or left half 504b) of image 502. Photomultiplier tube 174 can have, for example, the same characteristics as photomultiplier tube 110. A set of knife edges is used to block out the left half 504b (or the right half 504a) of the scattered laser light in the image 502. As the charged particles move in and out of the region in the ion trap 102 represented by the right half 504a (or left half 504b) of the image 502, the signal of the photomultiplier tube 174 alternates between detection of stronger and weaker scattered light. The oscillatory signal 602 generated by photomultiplier tube 174 has a frequency that is equal to the radial secular frequency $\omega_r$.

Referring to FIG. 7, a Fourier transform of the time-domain oscillatory signal 602 shows that the radial secular frequency of the diamond nanoparticle is about $2\pi \times 5$ Hz, i.e., $\omega_r/2\pi = 4.990 \pm 0.007$ Hz. The mass-to-charge ratio of the diamond nanoparticle can be calculated using the following equation:

$$m/z = \frac{V_{ac}}{\sqrt{2}\, \omega_r r_0^2 \Omega}, \quad \text{(Equ. 1)}$$

where $r_0$ is the radius of the ring electrode 112, $\Omega = 2\pi f$, f is the frequency of the audio frequency voltage applied between the ring electrode 112 and the end-cap electrodes 114, 116, and $V_{ac}$ is the amplitude of the audio frequency voltage when signal 602 was measured. Since the mass-to-charge ratio can be calculated, this diamond nanoparticle can subsequently serve as a calibrant for the single-particle mass spectrometer 100.

A dimensionless parameter $q_{eject}$ is calculated to assess the accuracy of m/z measurements made from the mass spectrometer 100. The parameter $g_{eject}$ is defined as $$q_{eject} = \frac{4 V_{eject}}{(m/z) r_0^2 \Omega^2}, \quad \text{(Equ. 2)}$$

where $V_{eject}$ is the amplitude of the audio frequency voltage signal when the charged particle inside the ion trap 102 becomes unstable and is ejected from the ion trap 102. The parameter $g_{eject}$ remains relatively constant for charged particles having different m/z ratios.

By combination of Equations 1 and 2, the parameter $q_{eject}$ can be written as, $$q_{eject} = \frac{V_{eject}}{V_{ac}} \frac{4\sqrt{2}\, \omega_r}{\Omega}, \quad \text{(Equ. 3)}$$

where $V_{ac}$ is the amplitude of the audio frequency voltage when the frequency $\omega_r$ was determined according to the method described in conjunction with FIGS. 5–7. In Equation 3, $g_{eject}$ depends on the ratio $V_{eject}/V_{ac}$ rather than on their absolute values. This allows fairly accurate measurement of parameter $g_{eject}$. Based on Equation 3 and repeated experiments, parameter $g_{eject}$ can be determined to be about $0.949 \pm 0.004$ when f is about 300 Hz. The value of parameter $q_{eject}$ varies only slightly (within experimental tolerances) with f ranging from 200 Hz to 600 Hz. This indicates that the mass spectrometer 100 can obtain a mass accuracy that is better than 0.5%.

The following are examples of measurements made from the single-particle mass spectrometer 100. The measurements show that the mass spectrometer 100 can be used in research of polystyrene microparticles, single diamond nanoparticles with a diameter of 100 nm, and DNA clusters of bacteriophage T4 with a molecular weight (M) larger than $10^8$ Da.

Amino-polystyrene particles

Referring to FIGS. 8a and 8b, single-particle mass spectra are obtained from samples derived from a colloidal suspension (product number AP-08-10 from Spherotech Inc., Libertyville, Ill.) containing 5.0% (weight by volume) monodisperse amino-polystyrene particles and 0.02% $NaN_3$. The particles have a mean diameter of $0.91 \pm 0.022$ μm. The particles are thoroughly washed with deionized water before the measurement to reduce contamination from electrolytes. The surfaces of these particles are functionalized with the aminoheptyl groups [—$(CH_2)_7 NH_2$] of $3 \times 10^6$ molecules/particle. The particles have a proton affinity of about 220 kcal/mol, similar to that of $CH_{3(CH2)6} NH_2$. Therefore, as the particles are introduced to the ion trap 102 in a positively charged spray, the surfaces of the particles should be predominantly covered with protons rather than other competing cations (e.g., $Na^+$). The colloidal suspension of amino-polystyrene microspheres was diluted to a concentration of 0.05% (weight by volume) in 4:1 $CH_3OH/H_2O$ and adjusted to pH=3.9 with acetic acids.

FIGS. 8a and 8b show two mass spectra acquired in two independent experiments using the same suspension and the trap driving frequency of $\Omega/2\pi = 600$ Hz. The two spectra look entirely different, with peaks nearly randomly distributed. The feature, together with the Gaussian-like distribution of the peak intensities, suggests that the individual peak in the observed mass spectrum is derived from one single particle. The data in FIGS. 8a and 8b were obtained from numerous measurements. In each measurement, about 10 particles were trapped and ejected in sequence from the ion trap 102. The aggregated data from the numerous measurements would be similar to data obtained from a single measurement where the sum of particles from each measurement were analyzed at the same time. For example, a histogram of the spectra acquired in 100 repetitions of the experiment (each experiment measuring 10 particles) is equivalent to the single spectrum that would be observed when an ion ensemble of 1,000 particles is analyzed at the same time using the single-particle mass spectrometer 100.

Graph 802 shows an enlarged view of a pulse having a full width at half maximum of $\Delta(m/z) = 4 \times 10^3$. The indicates that the mass spectrometer 100 can measure the mass of a particle with an accuracy of $\Delta m/m \approx 10^{-4}$.

Diamond nanocrystals

Figure 9:
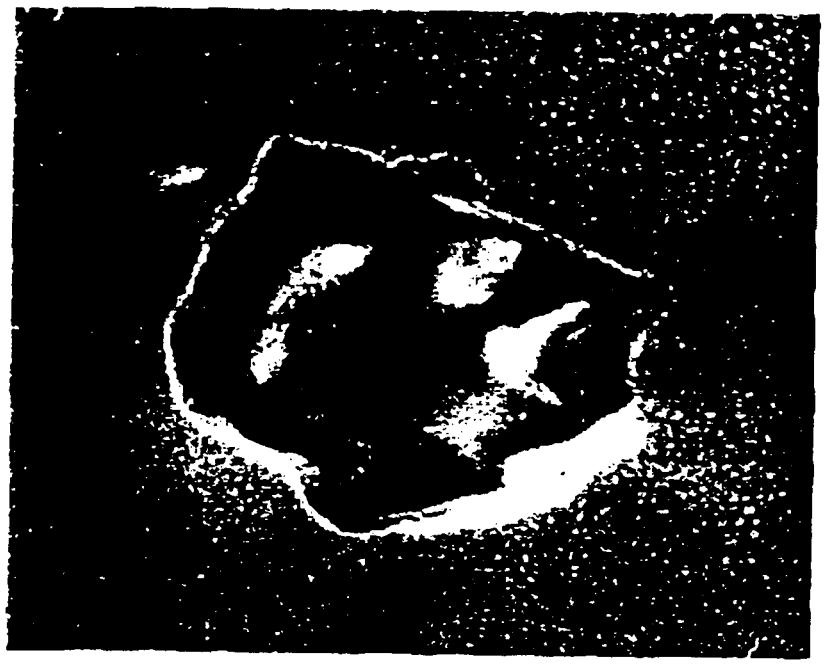
FIG. 9 is a photograph of a diamond nanocrystal taken using a transmission electron microscope.
Figure 10:
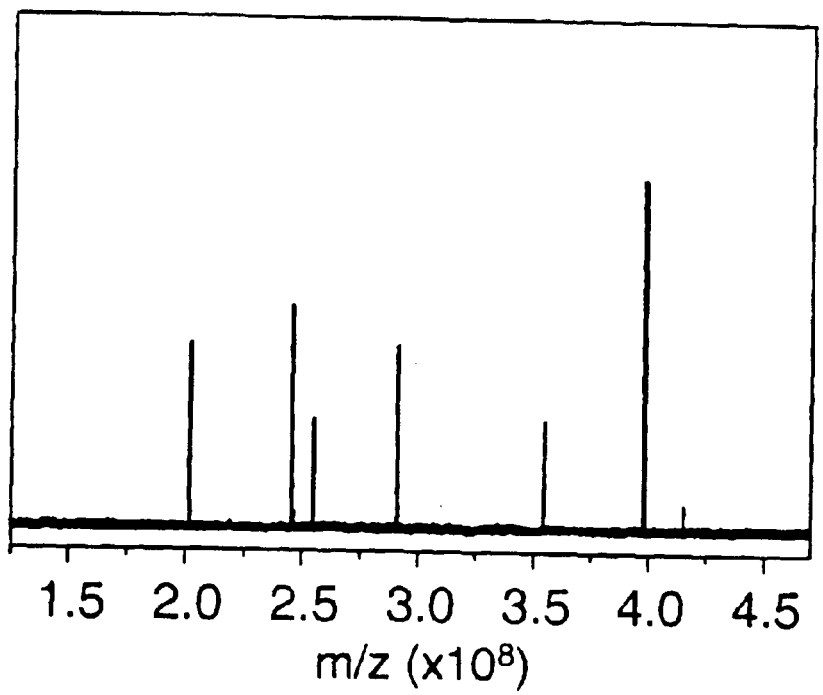
FIG. 10 is a graph showing a single-particle mass spectrum of diamond nanocrystals.

Referring to FIG. 9, a diamond nanocrystal is shown to have irregular shape. Referring to FIG. 10, a mass spectrum was obtained from a solution containing diamond nanocrystals (product number SJK-5 from Kay Industrial Diamond Corporation, Deerfield Beach, Fla.). The solution was first oxidized in air at 600° C. for one hour to ensure that their surfaces are covered with ether, carbonyl, or carboxylic groups. With these functional groups on the surfaces of the diamond nanocrystals, the nanocrystals are ready to accept protons from acetic acids during the electrospray ionization process. A 4:1 $CH_3OH/H_2O$ mixture containing 0.02% (weight by volume) of the nanocrystals adjusted to pH=3.9 is used as the spray solution in this measurement.

The diamond nanocrystals used to obtain the mass spectrum in FIG. 9 have irregular shapes and distinct sizes. Some of the nanocrystals have rough surfaces, while others are in the form of aggregates composed of smaller particles of about 40 nm in diameter. While the nanocrystals are nearly ten-fold smaller than the polystyrene microspheres discussed previously, a mass spectrum with a signal-to-noise ratio exceeding 20 can still be obtained. If each nanocrystal is estimated to have a mass of about $1.5 \times 10^{-17}$ kg with 100 nm diameter in size, then on average there are about 50 protons on each of these diamond nanocrystals.

DNA clusters

The mass spectrometer 100 may also be used to determine the molecular weight of biopolymers with a mass greater than $10^8$ Da. An example is the coliphage T4 DNA molecule. In aqueous solutions, the coliphage T4 DNA molecule has been determined to have a mass of about 110±4 MDa per molecule. Therefore, a cluster of these giant molecules has a mass-to-charge ratio within the range that can be measured by the mass spectrometer 100. Because the number of molecules and the number of charges are both integers, the molecular weight of the DNA molecules can be determined from a careful analysis of the single-particle mass spectra obtained using mass spectrometer 100. This approach is more direct than other complex methods adopted for measurement of the molecules in aqueous solutions.

Figure 11:
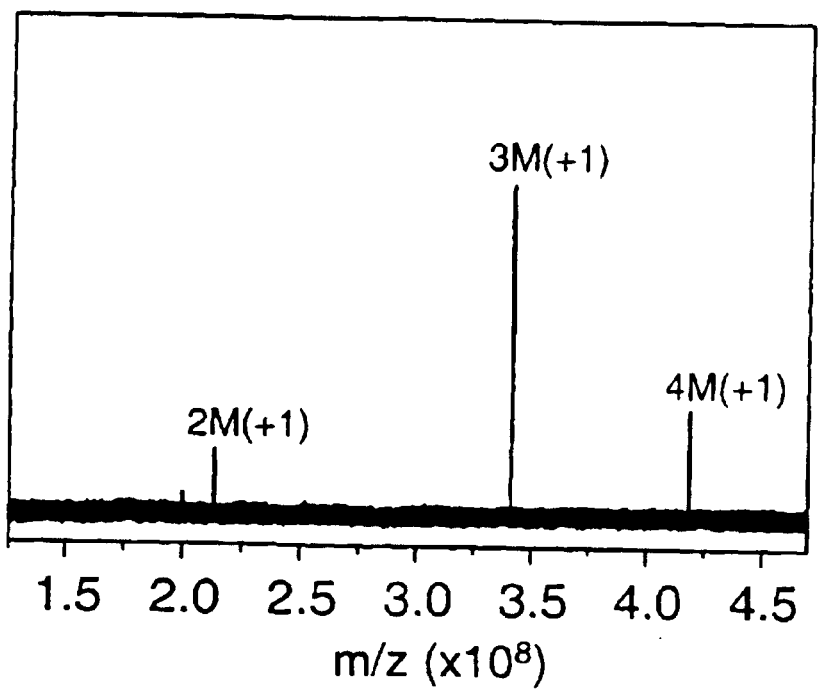
FIG. 11 is a graph showing a single-particle mass spectrum of coliphage T4 DNA clusters.

Referring to FIG. 11, a mass spectrum of coliphage T4 DNA molecules is shown. The DNA sample is suspended in a 1:3 $CH_3OH/H_2O$ solution with a concentration of 0.01% (weight by volume). In this suspension, the DNA molecules can form aggregates, as they are known to gel easily at high concentration. As can be seen in FIG. 11, there are three peaks in the spectrum that can be reasonably associated with singly charged dimer, trimer, and tetramer of the T4 DNA molecule. The mass of the T4 DNA molecules can be determined from the spectrum in FIG. 11 with an uncertainty of 4%.

A number of embodiments of the invention have been described. Nevertheless, it will be understood that various modifications may be made without departing from the spirit and scope of the invention. For example, methods other than using the electrospray ionization source 106 can be used to generate single charged particles to be analyzed by the ion trap 102. For example, matrix-assisted laser desorption and ionization can be used. The ion trap can be modified with a stretched geometry. The pressures given for the various chambers may be varied. The relative positions of the laser diodes 108, 184, the CCD camera 168, the photomultiplier tubes 110, 174 may be varied as long as light scattered from the particles can be detected. More efficient light collection methods using larger optics or multiple lenses can be implemented. Other methods of detecting particles ejected from the ion trap may be used. Accordingly, other embodiments are within the scope of the following claims.

What is claimed is:

1. Apparatus comprising:
   a first end-cap electrode, a second end-cap electrode, and a ring electrode positioned relative to the first end-cap electrode and second end-cap electrode to confine a charged particle from an ion source within a confinement region when an audio frequency voltage is applied between the ring electrode and the first end-cap electrode and second end-cap electrode at a first amplitude, and to eject the charged particle from the confinement region when the amplitude of the audio frequency voltage is increased to a second amplitude.

2. The apparatus of claim 1 wherein the first end-cap electrode includes an ion entrance aperture, the second end-cap electrode includes an ion ejection aperture, and the ring electrode include an observation aperture.

3. The apparatus claim 1, further comprising a light detection module that detects light scattered from the charged particle after it is ejected from the confinement region.

4. The apparatus of claim 1 wherein the ion source is positioned above the electrodes and includes a needle, a capillary, and a differential pumping region, the needle being aligned along a vertical axis above the capillary, the capillary being aligned along the vertical axis above the differential pumping region.

5. The apparatus of claim 4 wherein the capillary and the differential pumping region are electrically connected to electric ground and the needle is connected to a DC voltage.

6. The apparatus of claim 1 wherein the audio frequency voltage is in a frequency range between about 50 and 2000 hertz.

7. The apparatus of claim 1 wherein the charged particle has a mass in the range of about 1 mega-dalton to 10,000 mega-daltons.

8. The apparatus of claim 1 wherein the first amplitude is about 400 volts.

9. The apparatus of claim 8 wherein the second amplitude is greater than about 400 volts and less than about 1700 volts.

10. A method comprising:
    introducing a charged particle into an ion trap having a first end-cap electrode, a second end-cap electrode, and a ring electrode positioned between the first and second end-cap electrodes;
    applying an audio frequency voltage having a first amplitude between the ring electrode and the end-cap electrodes to generate an electromagnetic field that confines the charged particle within a confinement region; and
    increasing the amplitude of the audio frequency voltage to a second amplitude to eject the charged particle from the ion trap.

11. The method of claim 10, further comprising measuring a secular frequency of the motion of the charged particle inside the confinement region, and calculating a mass-to-charge ratio of the charged particle based on the second amplitude and the measured secular frequency.

12. The method of claim 10 wherein the audio frequency voltage is in a frequency range between about 50 and 2,000 hertz.

13. The method of claim 10 wherein the charged particle has a mass in the range of about 1 mega-dalton to 10,000 mega-daltons.

14. The method of claim 10, further comprising illuminating the ejected particle with a laser beam and detecting light scattered from the charged particle.

15. A mass spectrometer comprising:
    an ion source;
    an ion trap having:
    a first end-cap electrode, a second end-cap electrode, and a ring electrode positioned relative to the first and second end-cap electrodes to confine a charged particle from the ion source within a confinement region when an audio frequency voltage is applied between the ring electrode and the first and second end-cap electrodes at a first amplitude, and to eject the charged particle from the ion trap when the audio frequency voltage is applied between the ring electrode and the first and second electrodes at a second amplitude greater than the first amplitude; and a detection module configured to detect the charged particle after it is ejected from the ion trap.

16. The mass spectrometer of claim 15, further comprising an audio frequency power amplifier that generates the audio frequency voltage.

17. The mass spectrometer of claim 15 wherein the audio frequency voltage is in a frequency range between about 50 and 2,000 hertz.

18. The mass spectrometer of claim 15 wherein the first end-cap electrode includes an ion entrance aperture, the second end-cap electrode includes an ion ejection aperture, and the ring electrode includes an observation aperture.

19. The mass spectrometer of claim 15, wherein the detection module comprises a light source to illuminate the charged particle after it is ejected from the ion trap.

20. The mass spectrometer of claim 19 wherein the detection module further comprises a light detector that detects light scattered by the charged particle that is ejected from the ion trap.

21. The mass spectrometer of claim 15 wherein the ion source is positioned above the ion trap and includes a needle, a capillary, and a differential pumping region, the needle being aligned along a vertical axis above the capillary, the capillary being aligned along the vertical axis above the differential pumping region, the capillary and the differential pumping region being electrically connected to electric ground, and the needle being connected to a DC voltage.

22. Th mass spectrometer of claim 15 wherein the charged particle has a mass in the range of about 1 mega-dalton to 10,000 mega-daltons.

23. The mass spectrometer of claim 15 wherein a mass-to-charge ratio (m/z) of the charged particle is calculated using $$m/z = \frac{4V_{eject}}{q_{eject}\, r^2 \Omega^2},$$

where $V_{eject}$ is the value of the second amplitude, r is the radius of the ring electrode, $\Omega$ equals $2\pi$ times the frequency of the audio frequency voltage, and $q_{eject}$ is a calibration parameter characteristic of the ion trap.

24. The apparatus of claim 23 wherein the mass-to-charge ratio calculated using the equation $$m/z = \frac{4V_{eject}}{q_{eject}\, r^2 \Omega^2}$$

has an accuracy in the order of $10^{-4}$.

* * * * *